United States Patent
Henry et al.

(10) Patent No.: US 10,960,239 B2
(45) Date of Patent: Mar. 30, 2021

(54) HEADGEAR TENSIONING FOR RESPIRATORY MASK

(71) Applicant: ResMed Pty Ltd, Bella Vista (AU)

(72) Inventors: Robert Edward Henry, Sydney (AU); Philip Rodney Kwok, Sydney (AU); Philip John Gunning, Sydney (AU); Karthikeyan Selvarajan, Sydney (AU); James Morrison, Sydney (AU); Paul Anthony Green, Sydney (AU); Christopher Kingsley Blunsden, Sydney (AU); Gregory Robert Peake, Sydney (AU); Christopher John Baxter, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 930 days.

(21) Appl. No.: 15/648,580

(22) Filed: Jul. 13, 2017

(65) Prior Publication Data

US 2017/0304660 A1   Oct. 26, 2017

Related U.S. Application Data

(63) Continuation of application No. 11/902,509, filed on Sep. 21, 2007, now Pat. No. 9,744,385.

(30) Foreign Application Priority Data

Sep. 21, 2006  (AU) ................ 2006905236

(51) Int. Cl.
  *A62B 18/08* (2006.01)
  *A61M 16/06* (2006.01)

(52) U.S. Cl.
  CPC ....... *A62B 18/084* (2013.01); *A61M 16/0683* (2013.01); *A61M 2205/0216* (2013.01);
  (Continued)

(58) Field of Classification Search
  CPC ..... Y10T 24/45534; A42B 1/22; A42B 3/145; A44B 11/266
  (Continued)

(56) References Cited

U.S. PATENT DOCUMENTS 3,063,058 A    10/1962  Vollet
3,430,306 A *  3/1969  Tareau ............. A41F 1/00
                                        24/593.1
(Continued)

FOREIGN PATENT DOCUMENTS

JP    8-503631    4/1996
JP    2006-55517  3/2006
(Continued)

OTHER PUBLICATIONS

Japanese Office Action in related JP Appln. No. 2007-244240 (dated Jan. 31, 2012).

(Continued)

*Primary Examiner* — Rachel T Sippel
(74) *Attorney, Agent, or Firm* — Nixon & Vanderhye P.C.

(57) ABSTRACT

A patient interface assembly is configured to deliver pressurized gas to the patient's airways. The patient interface assembly includes a patient interface structure that is configured to sealingly engage the patient's face. The patient interface includes a receptacle. The patient interface assembly further includes headgear configured to support the patient interface structure on the patient's head. The headgear includes a clip that is receivable by the receptacle. The receptacle and the clip together form a multiple stage connection arrangement in which each of the multiple stages corresponds to an interlocked position of the clip in the receptacle. Each stage is associated with a corresponding range of headgear tension.

20 Claims, 6 Drawing Sheets

(52) U.S. Cl.
CPC .............. *A61M 2205/0227* (2013.01); *A61M 2205/0283* (2013.01); *A61M 2205/14* (2013.01); *A61M 2205/583* (2013.01)

(58) Field of Classification Search
USPC .............................................. 2/181, DIG. 11
See application file for complete search history.

(56) References Cited

U.S. PATENT DOCUMENTS

| | | | |
|---|---|---|---|
| 3,613,679 | A | 10/1971 | Bijou |
| 5,054,433 | A | 10/1991 | Pfleger |
| 5,416,279 | A | 5/1995 | Tseng |
| 5,779,659 | A | 7/1998 | Allen |
| 6,142,968 | A | 11/2000 | Pigg et al. |
| 6,152,893 | A | 11/2000 | Pigg et al. |
| 6,432,074 | B1 | 8/2002 | Ager et al. |
| 6,609,865 | B2 | 8/2003 | Daigneault |
| 7,156,918 | B2 | 1/2007 | Marks |
| 7,730,846 | B2 | 6/2010 | Pett et al. |
| 2002/0029780 | A1 | 3/2002 | Frater et al. |
| 2004/0112377 | A1 | 6/2004 | Amarasinghe et al. |
| 2005/0172969 | A1 | 8/2005 | Ging et al. |
| 2005/0199240 | A1* | 9/2005 | Hall .................. A61M 16/0825 128/206.26 |
| 2006/0042629 | A1 | 3/2006 | Geist |
| 2006/0174459 | A1* | 8/2006 | Bledsoe .................. A41F 1/008 24/634 |
| 2006/0217247 | A1 | 9/2006 | Potak et al. |
| 2007/0186931 | A1 | 8/2007 | Zollinger et al. |
| 2008/0083412 | A1 | 4/2008 | Henry et al. |
| 2009/0168612 | A1 | 7/2009 | Robin et al. |

FOREIGN PATENT DOCUMENTS

| | | |
|---|---|---|
| WO | 94/12133 | 6/1994 |
| WO | 2002/47749 | 6/2002 |
| WO | 2004/041341 | 5/2004 |
| WO | 2005/063326 | 7/2005 |
| WO | 2005/092676 | 10/2005 |
| WO | 2006/072128 | 7/2006 |

OTHER PUBLICATIONS

Shadow Air Muscles, Shadow Robot Company Ltd of UK, http://www.shadowrobot.com/airmuscles.
Dr. Yoseph Bar-Cohen, "ElectroActive Polymers—EAPs," The A to Z of Materials, www.azom.com/details.asp?ArticleID=885.
European Search Report, Appln. No. 07116993.2, dated Dec. 19, 2007, 7 pgs.

* cited by examiner

HEADGEAR TENSIONING FOR RESPIRATORY MASK

CROSS REFERENCE TO APPLICATIONS

This application is a continuation of U.S. application Ser. No. 11/902,509, filed Sep. 21, 2007, now allowed, which claims the benefit of Australian Provisional Application No. AU 2006905236, filed Sep. 21, 2006, each of which is incorporated herein by reference in their entirety.

BACKGROUND OF THE INVENTION

1. Field of the Invention

The present invention relates to a headgear assembly for use in holding a patient interface such as a respiratory mask in position on a patient's face, the patient interface being used in the treatment, e.g., of Sleep Disordered Breathing (SDB) with Non-Invasive Positive Pressure Ventilation (NIPPV).

2. Description of Related Art

Respiratory mask assemblies for treatment of SDB such as Obstructive Sleep Apnea (OSA) are typically secured to the patient's head by means of a headgear assembly.

Headgear assemblies are structured to position and stabilize a patient interface, such as a nasal mask, on a patient's face so that a good seal can be maintained. A headgear assembly typically includes a pair of side portions, and a rear portion. The side portions are adapted to engage with the patient's mask, and the rear portion is adapted to engage the back of the patient's head.

Prior art headgear arrangements typically have side straps typically held in position using hook and loop material, for example VELCRO®, by passing an end of the strap through a loop on the mask—or on a connector which connects to the mask—and then folding it back onto itself. In this way, the strap can be adjusted to adjust the headgear tension and thus the force which the headgear applies to hold the mask against the patient's face, to suit the particular needs of the patient in order that a comfortable effective mask seal be effected.

Correct adjustment of the headgear tension is important to the success of the therapies and to achieving patient compliance with the therapy regime.

Currently, patients generally use mask comfort to determine the headgear tension adjustment. However, the time period over which the patient is adjusting the tension is short in comparison with the length of each therapy session, and what feels comfortable over a 5 or 10 minute adjustment period will often be too tight to maintain comfort over an 8 hour therapy session. Also, changes in treatment pressure at the mask may require different headgear tension settings for optimal performance.

The ideal headgear tension is the loosest possible to maintain a seal between the mask cushion and the patient's face. However, it is intuitive for the patient to continue to tighten the headgear straps to seek to eliminate mask leak completely. In some instances, overtightening of the headgear may crush the sealing cushion of the mask and in fact increase the leak.

Furthermore, overtightening may cause patient discomfort, marking or creasing of the patient's face and neck which is visible the next day, and may lead to sores and tissue necrosis. Other possible effects of overtightening include dental and gum impairment, and pressure on the temporomandibular joints causing headaches, increased occurrence of apnea, or a reduction of nasal passage area leading to increased breathing resistance. All of these may make the therapy unpleasant for the patient and may lead to non-compliance with the therapy by the patient.

Alternatively, insufficient headgear tension may lead to mask leak by failure to maintain a seal between the mask and the patient's face, or movement of the mask while the patient sleeps, which may limit the success of the therapy or may wake the patient and lead to the patient discontinuing the therapy.

SUMMARY OF THE INVENTION

One aspect of the present invention relates to a headgear assembly for attachment to a patient interface that delivers breathable gas to a patient such as a respiratory mask to a patient's face, including a headgear body adapted to fit to the patient's head and has connection portions adapted for connection to the patient interface, adjustment means for adjusting said headgear, and indicating means responsive to an adjustment parameter of the headgear for indicating attainment of a desired adjustment setting of the headgear.

Another aspect of the invention relates to a patient interface adapted to deliver breathable gas to a patient and adapted for attachment to the patient by means of adjustable headgear, including indicating means responsive to an adjustment parameter of the headgear for indicating attainment of a desired adjustment setting of the headgear.

Another aspect of the invention relates to a headgear assembly for attachment to a patient interface that delivers breathable gas to a patient, including:

a headgear body adapted to fit to the patient's head and having connection portions adapted for connection to the patient interface;

an adjustment mechanism to adjust the headgear body, and a limiter to limit tightening adjustment of the headgear body.

Another aspect of the invention relates to a headgear assembly for attachment to a patient interface that delivers breathable gas to a patient, including:

a headgear body adapted to fit to the patient's head and having connection portions adapted for connection to the patient interface, an adjustment mechanism to adjust the headgear body, and a control mechanism to control adjustment of headgear tension.

Another aspect of the invention relates to a method for controlling adjustment of headgear. The method includes adjusting the headgear and visually indicating attainment of a desired adjustment setting of the headgear.

Another aspect of the invention relates to a connector arrangement for a patient interface. The connector arrangement includes a connector provided to a mask and a clip provided to headgear. The clip is adapted to connect to the connector in a multiple stage arrangement such that release of the clip from one stage to an adjacent stage indicates attainment a desired headgear tension.

Another aspect of the invention relates to headgear for a patient interface. The headgear includes at least one headgear strap and an indicator provided to the at least one headgear strap structured to indicate attainment of a desired adjustment setting of the headgear in response to headgear tension applied to the at least one headgear strap.

Another aspect of the invention relates to a connector arrangement for a patient interface. The connector arrangement includes a connector provided to a mask and a clip provided to headgear. The clip is adapted to connect to the connector such that excessive tension applied to the clip allows the clip to completely release from the connector.

Another aspect of the invention relates to a method for controlling headgear tension. The method includes connecting headgear straps of headgear to a mask and releasing tension upon application of excessive tension force to the headgear straps.

Further aspects of the invention relate to a patient interface and headgear combination, and a method of controlling adjustment of a headgear for a patient interface.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
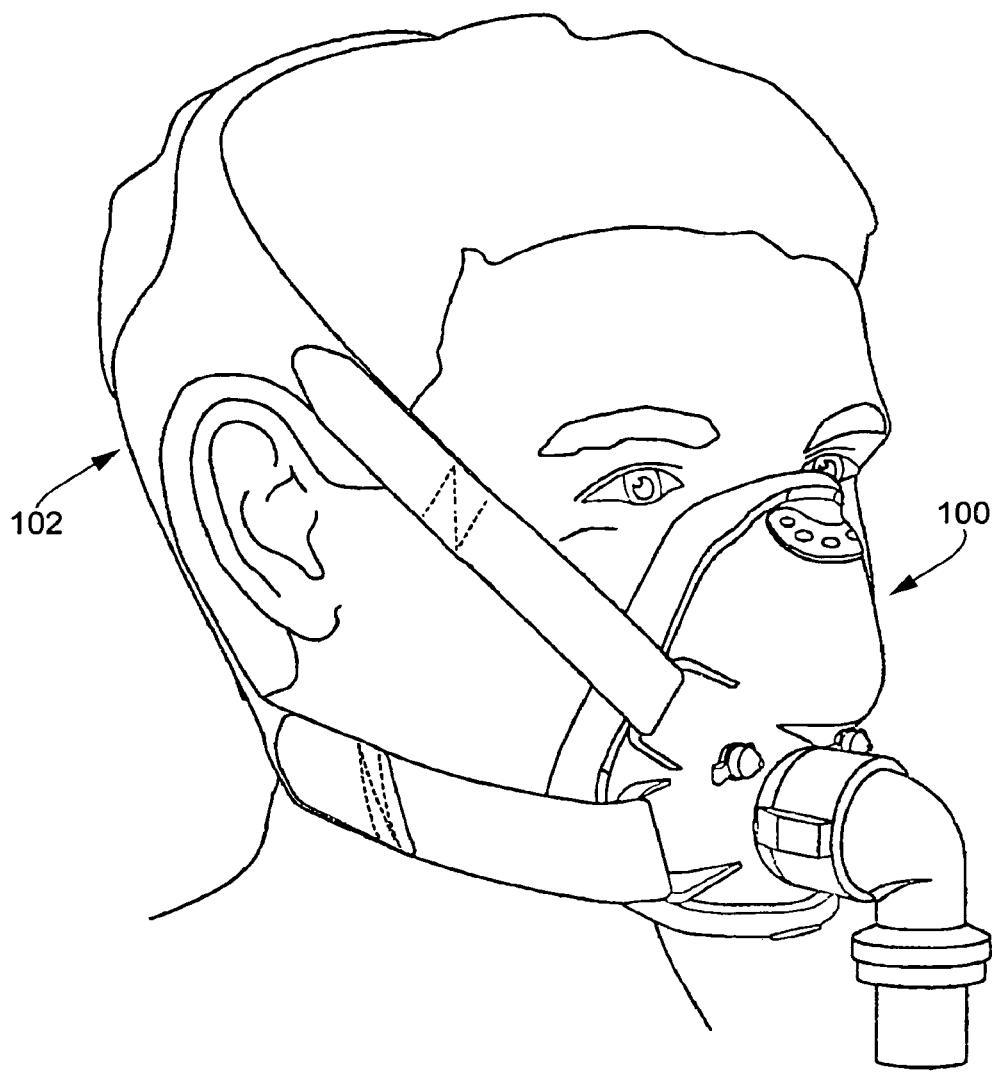
FIG. 1 is a front perspective view of a prior art MIRAGE® full face headgear and mask arrangement.

FIG. 1 shows the Applicant's prior art MIRAGE® full face mask 100 and headgear 102 according to the Applicant's PCT Application WO 02/47749, which is incorporated herein by reference in its entirety.

The mask 100 is connected to a positive airway pressure (PAP) device or flow generator device (not shown) which provides breathable gas to the mask for treatment of sleep apnea.

Figure 2:
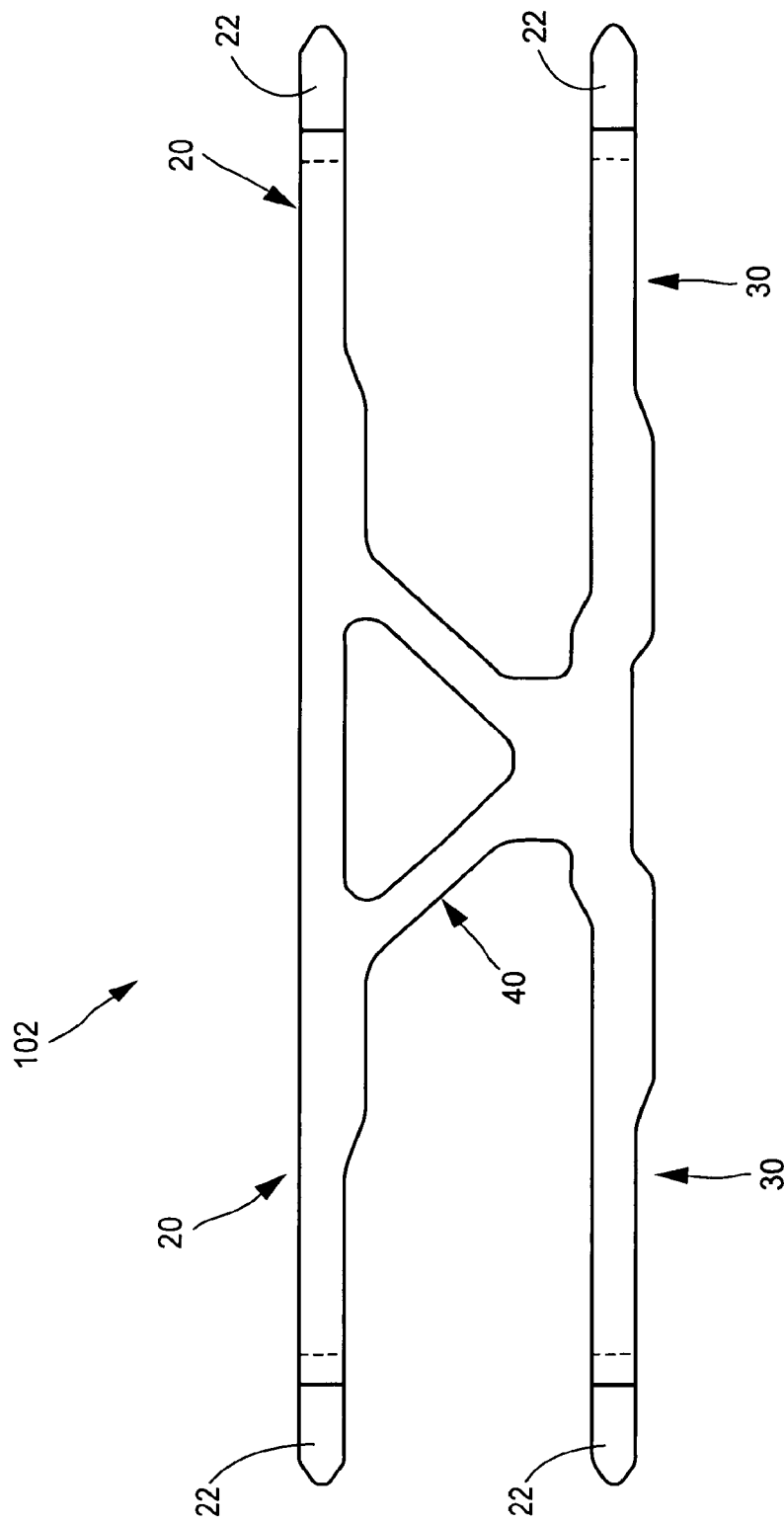
FIG. 2 is the MIRAGE® headgear arrangement of FIG. 1 when laid flat.

As shown in FIG. 2, the headgear 102 is constructed from a composite of polyurethane foam, loop material and hook material whose shape includes a pair of upper straps 20 and lower straps 30 and a generally triangular back portion 40. A piece of hook material 22 (e.g., such as Velcro®) is attached to the end of each of the four straps so that the straps may be secured to attachment points on the mask 100.

The hook material 22 may be 'one way' hook material so that it does not catch on itself in the process of overlaying the straps before they are brought into engagement.

In other, unillustrated, prior art arrangements, the straps 20, 30 may be adapted to fit to a male clip connector which clips into a female connector moulded into the mask frame of mask 100.

Figure 3:
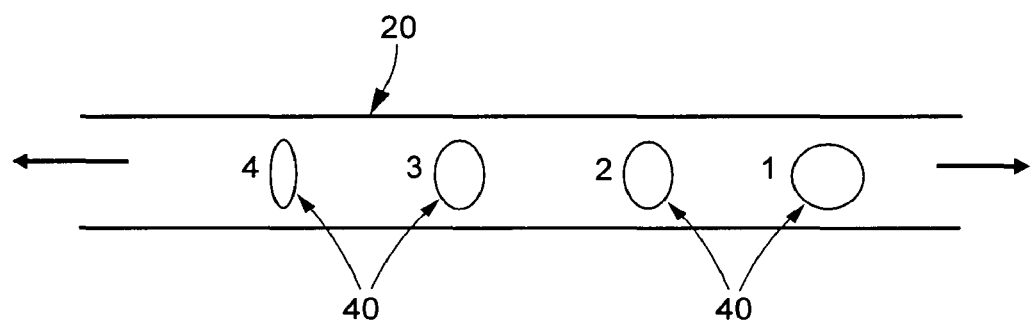
FIG. 3 is a schematic view of a set of visible indicia for indicating the headgear tension according to one embodiment of the invention.

FIG. 3 shows a set of visible indicia 40 which may be printed onto or otherwise formed on the headgear 102, e.g., on the side straps 20, 30 or elsewhere on the headgear which is visible to the wearer in a mirror.

The indicia 40 comprise a set of ellipses of successively greater aspect ratios, having vertical major axes. The indicia 40 may be labelled with tension settings, e.g., 1, 2, 3, 4, etc. In an embodiment, the indicia may be labelled in mirror image so that they are readable by the wearer in the mirror. It should be appreciated that any suitable number of ellipses may be provided, and the ellipses may be spaced apart from one another in any suitable manner to indicate the setting.

In one alternative form of this embodiment, the setting labels may indicate treatment pressures for which the corresponding headgear adjustment setting is recommended.

As the headgear strap (e.g., strap 20 of headgear 102) is placed under tension by tightening of the headgear (tension indicated by arrows), the headgear material stretches in the direction normal to the ellipse axes and the ellipses become more circular. As the tension increases, first one then the next ellipse become approximately circular, with the most circular ellipse indicating the tension setting. The wearer adjusts the headgear until the desired tension setting is reached. That is, ellipse 1 will become circular as tension is initially applied, ellipse 2 will become circular as more tension is applied, etc., with ellipse 4 becoming circular at the highest tension setting.

Figure 4A:
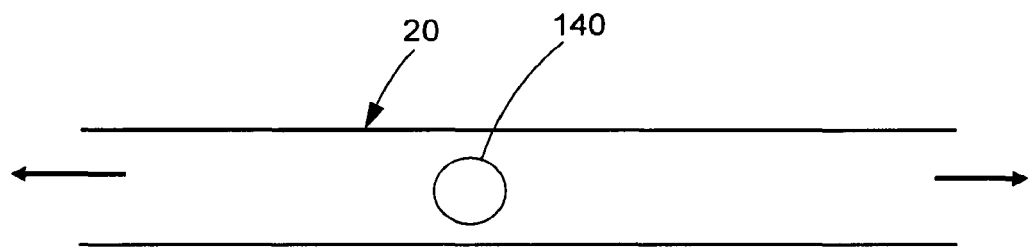
FIGS. 4A and 4B are schematic views of visual indicia indicating attainment of the desired headgear tension according to another embodiment of the invention.
Figure 4B:
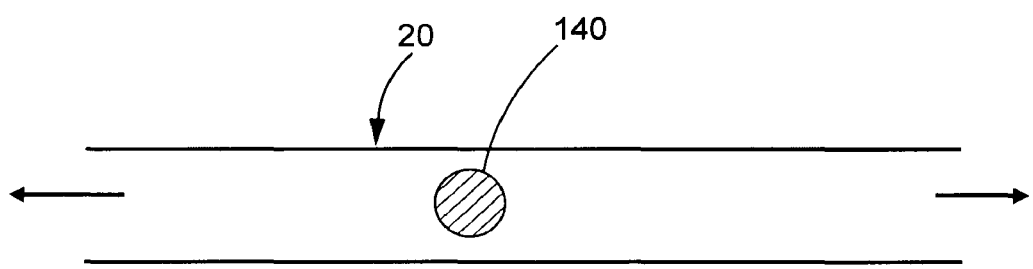

In a further embodiment shown in FIGS. 4A and 4B, the indicia 140 are formed on the side straps 20,30 by printing on the underlying material of the headgear which is covered by a top layer. When the headgear is not tensioned, the indicia 140 are obscured by the top layer (FIG. 4A), but when the desired headgear tension is reached the material of the top layer becomes see-through and the indicia 140 become visible (FIG. 4B).

Figure 5:
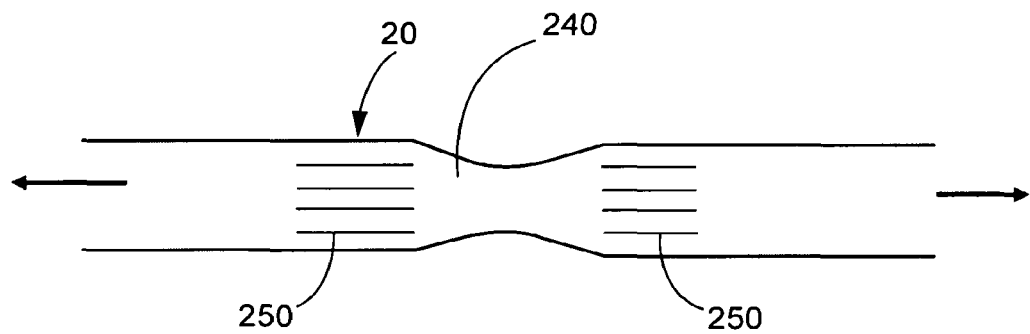
FIG. 5 shows a necking portion on the headgear according to another embodiment of the invention.

In an embodiment shown in FIG. 5, the headgear straps 20,30 may include a necked portion 240 which narrows as the headgear tension is increased, and markings 250 may be provided adjacent the necked portion 240 for assessing the headgear tension. For example, the markings 250 provide a reference for how narrow the necked portion 240 becomes upon tension.

Figure 6A:
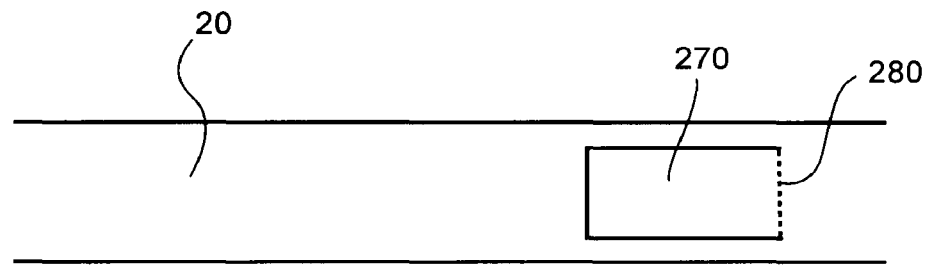
FIGS. 6A to 6C show a further embodiment of the invention using relative movement between an underlying and overlying portion of the headgear to indicate adjustment.
Figure 6B:
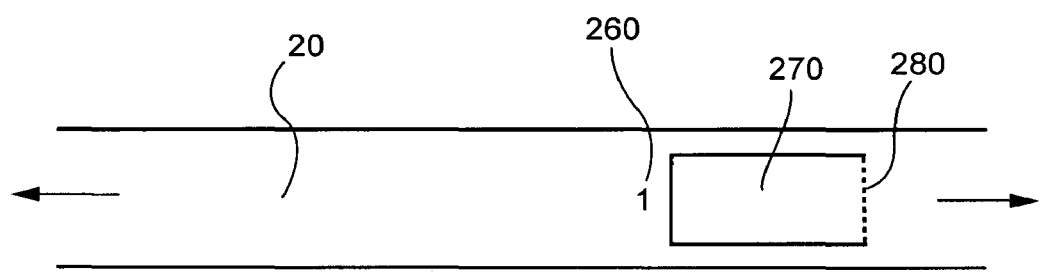
Figure 6C:
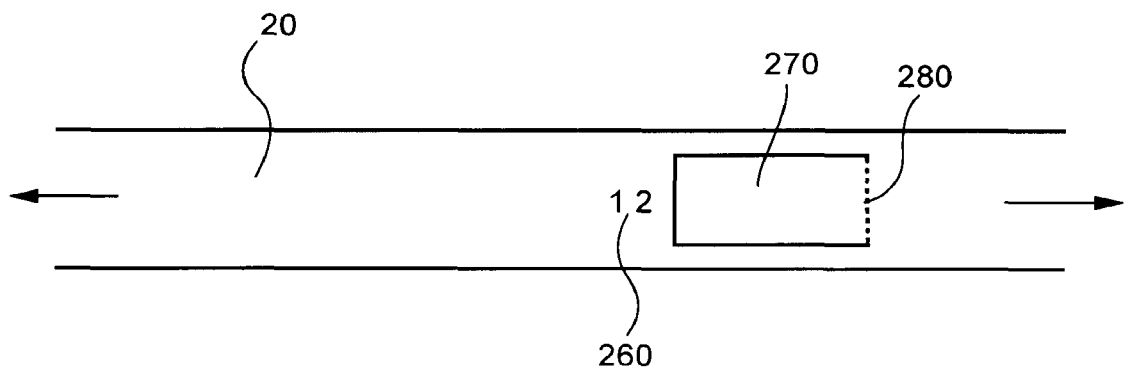

FIGS. 6A to 6C illustrate a further embodiment of indicia 260 on the headgear, in the form of a series of numerals or other symbols indicating adjustment settings. The headgear also has a cover flap 270 attached to the surface of the headgear strap (e.g., strap 20) along a fold line 280. The flap obscures the indicia 260 when the headgear is untensioned (FIG. 6A). The headgear material stretches as tension is applied (tension indicated by arrows), with the relative movement between the indicia 260 and the cover flap 270 causing the indicia 260 (e.g., numerals such as 1, 2, 3, etc.) progressively being uncovered as the tension increases. The highest value uncovered numeral indicates the adjustment setting of the headgear. That is, the numeral 1 is uncovered as tension is initially applied (FIG. 6B), numeral 2 is uncovered as more tension is applied (FIG. 6C), etc., with the highest numeral becoming uncovered at the highest tension setting.

In a further unillustrated embodiment, the indicia may comprise an contact pressure film located between the rim and cushion of the mask, which changes colour with changes to the pressure on the seal as the headgear is tightened or otherwise adjusted. The film may provide an indication of excessive pressure between the mask rim and the seal, and the dispersion of that pressure. Examples of suitable contact pressure films include Pressurex tactile force indicating films from Sensor Products Inc of USA., and FilmLOC colour changing PET film from Austik Technologies of USA.

Further headgear tension sensing means may include electrical sensors such as strain gauges or capacitance sensors which vary capacitance depending on the distance between the capacitor plates. The sensor readings are fed back to the flow generator, the processor of which is programmed with an algorithm for converting the signal into a tension setting for display on the flow generator display, and/or to provide an audible or visible signal when the desired headgear tension is reached.

Further aspects of the invention relate to tightening mechanisms for adjustment of the headgear tension.

In one embodiment, the side straps 20,30 may be connected to the mask by means of connectors which clip onto the mask frame of mask 100. The connection between the mask and the headgear connectors is adapted to provide a visual, tactile or audible signal on reaching the desired tension, and/or to release when the desired tension is exceeded.

FIGS. 7A to 7D schematically illustrate the operation of a clip 300 provided to side straps 20,30 of the headgear and a connector 330 provided to the mask frame of mask 100, according to one embodiment of the invention.

The connector 330 (in the form of a female connector or clip receptacle) on the mask frame has a pair of opposed sides 332 each with inward projections 334 having a sloping front surface 336 and a more upright rear surface 338.

The clip 300 has a body 302 and a pair of spring arms 304 with outward projections, i.e., front projection 306 and centre projection 308 which form two recesses 310, 312 for receiving the projections 334 of the connector 330.

Figure 7A:
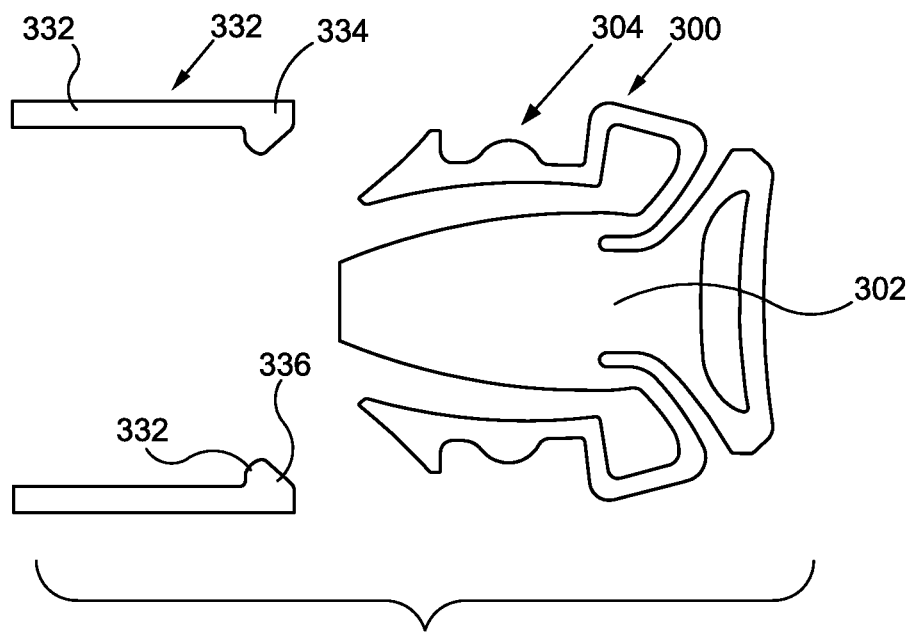
FIGS. 7A to 7D show a clip and catch arrangement according to a further embodiment of the invention.
Figure 7B:
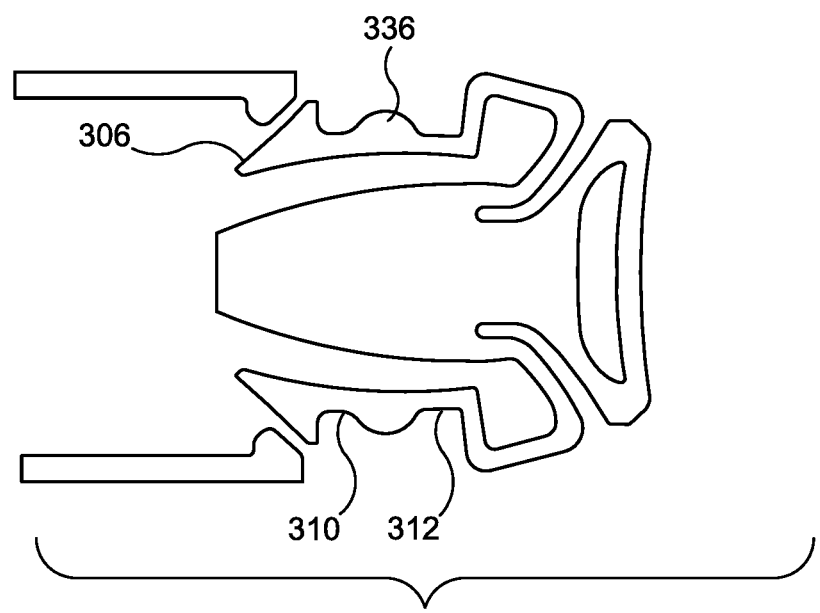
Figure 7C:
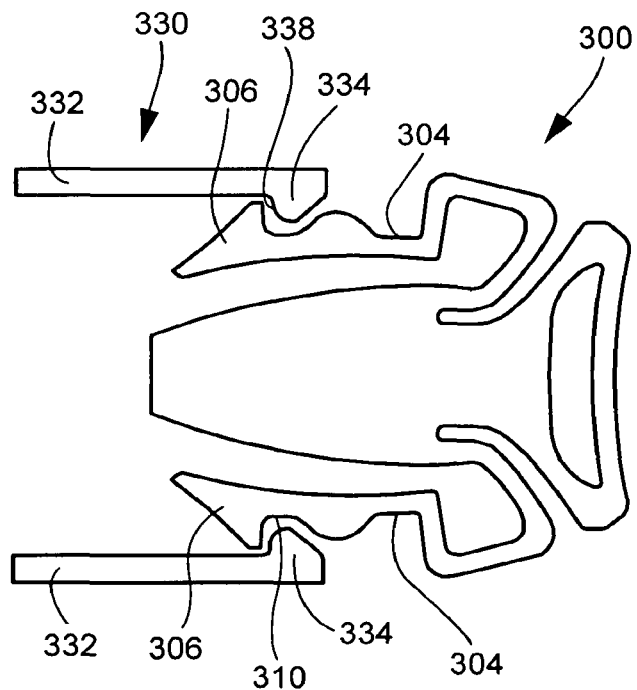
Figure 7D:
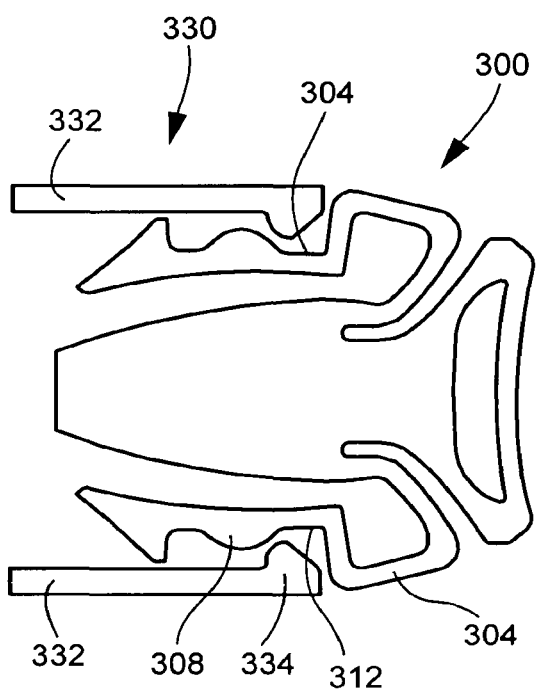

The clip connection comprises a two stage latch arrangement in which the clip 300 clicks into the connector 330 on the mask in a first stage connection in which the clip travels from the position of FIG. 7A to that in FIG. 7D. The clip will provide two audible and/or tactile clicks, i.e., one as it moves from the position of FIG. 7B to 7C and another when moving from the position of FIG. 7C to FIG. 7D.

For example, the clip 300 is engaged with connector 330 so that the sloping front surface 336 of the inward projections 334 engage the front projections 306 to flex the spring arms 304 inwardly towards the body 302 until the front projections 306 move past the inward projections 334 and into the position of FIG. 7C. As illustrated, the spring arms 304 resiliently return to its initial position so that the inward projections 334 extend into the recess 310 and the front projections 306 are retained by the rear surface 338. Further movement of the clip 300 into the connector 330 causes the center projection 308 to ride over the inward projections 334 and into the position of FIG. 7D, in which the inward projections 334 extend into the recess 312.

The user then starts to tighten the headgear using the hook and loop tabs on the side straps 20,30. As the user continues to tighten the headgear, the desired tension is reached and the spring arms 304 flex inwards so that the centre projections 308 ride past the projections 334 of the connector and the clip releases to the position of FIG. 7C, emitting an audible 'click' or other cue for the user to stop tightening the headgear. The user therefore knows that the appropriate headgear tension has been reached and may then fasten the hook material tabs to fix the headgear in this adjustment setting.

The release tension for which the clip is designed may be controlled by varying the stiffness of the spring arms 304 and the face angle and height of the centre projections 308.

Optionally, the clip connectors may be interchangeable for similar clips having different release tensions, so that the headgear tension, may be varied according to the treatment pressure and the patient's requirements or preferences.

In an embodiment, the clip and connector may be structured such that excessive tension applied to clip allows the clip to completely release from the connector. This quick release arrangement allows the patient to quickly remove the mask without manually flexing the spring arms, e.g., for emergency situation, panic situation, claustrophobia, to prevent excessive tension applied to the straps, which could be uncomfortable or even be harmful to the patient, etc. The release force may be controlled, e.g., by varying the stiffness of the spring arms, the face angle of the rear surface 338 of the inward projections 334, and/or the face angle of the rear surface of the front projections 306 (i.e., the surface of the front projection 306 adapted to face and/or engage the rear surface 338 when the clip is coupled to the connector). This quick release arrangement may be used with the multiple stage arrangement discussed above, or this quick release arrangement may be used independently.

Further tightening mechanisms according to embodiments of the invention include the use of piezo materials or artificial muscles (e.g., devices which contract lengthwise upon activation, for example of the types used in robotic control systems) incorporated into the rear or side portions of the headgear.

One example of a suitable artificial muscle apparatus is one or more pneumatic muscles incorporated into the headgear, i.e., tubular portions which contract lengthwise upon inflation, which may be inflated by air pressure from the flow generator. Examples of suitable air muscles include the Shadow Air Muscles available from Shadow Robot Company Ltd of UK and described at the website http://www.shadowrobot.com/airmuscles.

Alternative artificial muscle apparatus which may be employed include electro-active polymers (EAPs) which contract upon application of electrical energy. Suitable electro-active polymers may include electronic or ionic, with electronic EAPs being preferred due to ability to hold strain with DC activation and their relatively high actuation forces. Examples of electronic EAPs include ferroelectric polymers such as poly(vinylidene fluoride), dielectric EAPs having low elastic stiffness and high dielectric constants (also known as electrostatically stricted polymers or ESSPs), electrostrictive graft elastomers, electrostrictive papers, electro-viscous elastomers or liquid crystal elastomer (LCE) materials. Examples of ionic EAPs include ionic polymer gels, ionomeric polymer-metal composites, conductive polymers or carbon nanotubes. Further discussion of each of these types of EAPs may be found in the article "Electro-Active Polymers—EAPs" at the website "The A to Z of Materials", by Dr. Yoseph Bar-Cohen, at www.azom.com/details.asp?ArticleID=885, the contents of which article are incorporated herein by reference.

A yet further automated headgear adjustment mechanism includes a magnetic adjustment mechanism, for example by varying the distance between magnets of constant field strength, such as permanent magnets, or by varying the field strength of electromagnetic apparatus.

A further headgear adjustment mechanism includes a bladder mounted on or incorporated in the headgear, or a plurality of such bladders at different locations on the headgear, inflatable to increase the headgear tension. In one exemplary form, the bladder or bladders are inflated by air delivered by the flow generator. In one embodiment, the bladder or bladders are formed by comoulding with the material of the headgear.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface assembly configured to deliver pressurized gas to a patient's airways, the patient interface assembly comprising:
   a patient interface structure configured to sealingly engage the patient's face and including a receptacle; and
   headgear configured to support the patient interface structure on the patient's head, the headgear including a clip that is receivable by the receptacle,
   wherein the receptacle and the clip together form a multiple stage connection arrangement in which each of the multiple stages corresponds to an interlocked position of the clip in the receptacle, and
   wherein each stage is associated with a corresponding range of headgear tension, and
   wherein the clip is configured to be pulled from one stage to an adjacent stage in response to a headgear tension reaching a first threshold tension.

2. The patient interface assembly of claim 1, wherein the clip is configured to provide an audible and/or tactile feedback as the clip moves from one stage to another stage.

3. The patient interface assembly of claim 1, wherein the receptacle includes opposed sides, each opposed side comprising an inward projection, and wherein the clip includes at least one spring arm having a plurality of projections that form adjacent recesses.

4. The patient interface assembly of claim 3, wherein the multiple stage connection arrangement is configured so that when the clip and the receptacle are engaged, the inward projections of the opposed sides of the receptacle move between adjacent recesses in response to a change in headgear tension.

5. The patient interface assembly of claim 1, wherein the multiple stage connection arrangement is configured so that the clip and the receptacle separate when headgear tension is greater than a second threshold tension that is greater than the first threshold tension.

6. A patient interface assembly configured to deliver pressurized gas to a patient's airways, the patient interface assembly comprising:
   a patient interface structure configured to sealingly engage the patient's face and including a receptacle; and
   headgear configured to support the patient interface structure on the patient's head, the headgear including a clip that is receivable by the receptacle,
   wherein the receptacle and the clip together form a two-stage connection arrangement in which a first stage corresponds to a first interlocked position of the clip in the receptacle and a second stage correspond to a second interlocked position of the clip in the receptacle,
   wherein the first and second interlocked positions are arranged so that when the clip exits the first stage, the clip must enter the second stage, and
   wherein the clip is configured to be pulled from the first stage to the second stage in response to a headgear tension reaching a first threshold tension.

7. The patient interface assembly of claim 6, wherein the clip is configured to provide an audible and/or tactile feedback as the clip moves from the first stage to the second stage.

8. The patient interface assembly of claim 6, wherein the first stage is associated with a first headgear tension and the second stage is associated with a second headgear tension that is greater than the first headgear tension.

9. The patient interface assembly of claim 6, wherein the two-stage connection arrangement is configured so that the clip and the receptacle separate when headgear tension is greater than a second threshold tension that is greater than the first threshold tension.

10. The patient interface assembly of claim 6, wherein the clip is inserted further into the receptacle when the clip is in the first stage than when the clip is in the second stage.

11. The patient interface assembly of claim 6, wherein first and second interlocking positions are arranged so that the two-stage connection arrangement must be in the second stage before entering the first stage.

12. A patient interface assembly configured to deliver pressurized gas to a patient's airways, the patient interface assembly comprising:
   a patient interface structure configured to sealingly engage the patient's face and comprising a receptacle with opposed sides that each includes an inward projection; and
   headgear configured to support the patient interface structure on the patient's head, the headgear comprising a clip that is receivable by the receptacle and includes at least one spring arm having a first projection and a second projection that respectively form first and second recesses,
   wherein the receptacle and the clip together form a two-stage latch arrangement that is in a first stage when the inward projections of the opposed sides of the receptacle are in the first recess,
   wherein the two-stage latch arrangement is in a second stage when the inward projections of the opposed sides of the receptacle are in the second recess, and wherein the two-stage latch arrangement is configured to be pulled from the first stage to the second stage in response to a headgear tension reaching a first threshold tension.

13. The patient interface assembly of claim 12, wherein the clip is configured to provide an audible and/or tactile feedback as the two-stage latch arrangement moves from the first stage to the second stage.

14. The patient interface assembly of claim 12, wherein the at least one spring arm is configured to resiliently flex inwardly when the inward projections of the opposed sides of the receptacle engage any of the first and second projections.

15. The patient interface assembly of claim 14, wherein the second projection prevents the inward projections of the opposed sides of the receptacle from entering the second recess when headgear tension is less than the first threshold tension.

16. The patient interface assembly of claim 15, wherein the second projection prevents the inward projections of the opposed sides of the receptacle from exiting the second recess when headgear tension is less than a second threshold tension that is greater than the first threshold tension.

17. The patient interface assembly of claim 15, wherein the first and second recesses are arranged so that the inward projections of the opposed sides of the receptacle must enter the second recess after exiting the first recess.

18. The patient interface assembly of claim 12, wherein the clip is inserted further into the receptacle when the inward projections of the opposed sides are in the first recess than when the inward projections of the opposed sides are in the second recess.

19. The patient interface assembly of claim 12, wherein the first and second recesses are arranged so that the inward projections of the opposed sides of the receptacle must enter the second recess before entering the first recess.

20. The patient interface assembly of claim 12, wherein the first projection on the at least one spring arm has a different shape than the second projection on the at least one spring arm.

\* \* \* \* \*